United States Patent [19]

Bernstein

[11] Patent Number: 4,607,101

[45] Date of Patent: Aug. 19, 1986

[54] METHOD OF TREATING ACNE VULGARIS WITH A COMPOSITION CONTAINING CARBAMIDE PEROXIDE

[75] Inventor: Joel E. Bernstein, Deerfield, Ill.

[73] Assignee: Jaye-Boern Laboratories, Inc., Northbrook, Ill.

[21] Appl. No.: 594,405

[22] Filed: Mar. 27, 1984

Related U.S. Application Data

[63] Continuation of Ser. No. 296,920, Aug. 27, 1981, abandoned.

[51] Int. Cl.[4] .................... A61K 31/17; A61K 31/70
[52] U.S. Cl. ...................... 514/24; 514/859; 514/29; 514/154; 514/356; 514/588
[58] Field of Search ................... 514/24, 588

[56] References Cited

U.S. PATENT DOCUMENTS

| | | | |
|---|---|---|---|
| 2,430,450 | 11/1947 | Brown et al. | 424/322 |
| 2,542,897 | 2/1951 | Brown et al. | 424/322 |
| 2,542,898 | 2/1951 | Brown et al. | 424/322 |
| 3,372,125 | 3/1968 | Hill | 252/99 |
| 3,384,542 | 5/1968 | Acceha | 424/130 |
| 3,532,206 | 11/1970 | Taub et al. | 424/199 |
| 3,577,521 | 5/1971 | Scheller et al. | 424/55 |
| 3,657,413 | 4/1972 | Rosenthal | 424/81 |
| 4,163,800 | 8/1979 | Wickett et al. | 424/326 |
| 4,189,501 | 2/1980 | Fulton | 424/338 |
| 4,302,441 | 11/1981 | Mühlmann et al. | 424/48 |

FOREIGN PATENT DOCUMENTS

| | | |
|---|---|---|
| 2417872 | 10/1974 | Fed. Rep. of Germany . |
| 1555 | of 1912 | United Kingdom . |
| 964444 | 7/1964 | United Kingdom . |

OTHER PUBLICATIONS

Handbook of Non-Prescription Drugs, 5th Ed., 1977, p. 319.

*Primary Examiner*—Leonard Schenkman
*Attorney, Agent, or Firm*—Ronald A. Sandler; Jerry A. Schulman

[57] ABSTRACT

An improved method of treating acne vulgaris comprising administering a therapeutically effective amount of carbamide peroxide alone or in combination with one or more of a topical antibiotic, nicotinic acid or nicotinamide and compositions useful in said method.

11 Claims, No Drawings

METHOD OF TREATING ACNE VULGARIS WITH A COMPOSITION CONTAINING CARBAMIDE PEROXIDE

This is a continuation of application Ser. No. 296,920, filed Aug. 27, 1981, now abandoned.

BACKGROUND OF THE INVENTION

Acne vulgaris is an inflammatory disease of the pilosebaceous glands characterized by an eruption of the skin, often pustular in nature but not suppurative. Acne is a common affliction of the adolescent and affects a small but significant percentage of the adult population. Acne lesions are of four basic types: comedones (blackheads or whiteheads), papules, pustules, and cysts (or nodules). Various topical agents are utilized in the treatment of acne and these include sulfur, resorcinol, salicylic acid, benzoyl peroxide, vitamin A acid and topical antibiotics. Acne involvement results in unslightly lesions, particularly on the face, and in some cases results in severe scarring.

There are a variety of methods for treating acne vulgaris including topically applying various scrubbing or abrasive compositions, topically applying deep cleaning or astringent compositions and also exposure to ultraviolet radiation. Nevertheless, acne vulgaris is seldom cured and only can be contained with difficulty. Carbamide peroxide is an agent used to soften earwax for removal (Debrox ® Drops (International Pharmaceutical Corporation, 9233 Ward Parkway, Kansas City, Mo. 64114); Ear Drops by Murine (Abbott Laboratories, North Chicago, Ill. 60064) and to provide cleansing action in the oral cavity (Gly-Oxide ® Liquid (International Pharmaceutical Corporation, 9233 Ward Parkway, Kansas City, Mo. 64114).

In treating two young adults with Debrox ® Drops to cleanse their ears of earwax, I noted that blackheads, whiteheads, and some acne papules and pustules in front of ears cleared rapidly. I thought this might have resulted from spillage out of the ear or inadvertent application of the eardrops to these areas. Subsequently I tested topical formulations containing carbamide peroxide for effectiveness in acne and found surprisingly that carbamide peroxide applied topically to the skin is useful in the treatment of acne vulgaris. Also, surprisingly carbamide peroxide achieves such beneficial effects without much of the irritating and sensitizing effects of benzoyl peroxide. I have also found that combinations of carbamide peroxide with certain chemical agents known to be effective in treating acne are more effective in treating acne than would be expected by treatment with the individual agents themselves. Such formulations include combinations of carbamide peroxide and one or more of nicotinamide or topical anbitiotics such as erythromycin base, clindamycin phosphate and tetracycline hydrochloride.

SUMMARY OF THE INVENTION

The present invention provides an improved method of and composition for the treatment of acne vulgaris involving the periodic application of an effective amount of carbamide peroxide alone or in combination with one or more nicotinic acid or nicotinamide or topical antibiotics such as erythromycin base, clindamycin phosphate and tetracycline hydrochloride.

DETAILED DESCRIPTION OF PREFERRED EMBODIMENTS

In the practice of this invention, topical solutions of carbamide peroxide in various organic vehicles such as a combination of ethyl alcohol and propylene glycol in which the active ingredient is present in the range of from about 1% to about 15% by volume of the carrier are prepared.

Additionally topical solutions of carbamide peroxide in various organic carriers in concentrations ranging from 1 to 15% by volume of the carrier are incorporated into various organic vehicles including solutions, lotions, creams, gels, and ointments along with one or more of the following ingredients: nicotinic acid or nicotinamide in concentrations of from 1% to 10% by volume of the carrier; erthromycin base in concentrations of from 1% to about 6% by volume of the carrier; clindamycin phosphate in concentrations of from 1 to 5% by volume; tetracycline hydrochloride in concentrations of from 1 to 5% by volume of the carrier. Such carriers useful for the incorporation of carbamide peroxide include combinations of ethyl alcohol and propylene glycol as well as surface active agents such as lauryl ethers and lauryl esters. Applications of the carrier and effective ingredient are made to the face of acne patients 2 to 4 times daily with the result that open and closed comedones (blackheads and whiteheads) are markedly reduced within two weeks. The following examples illustrate the present invention.

EXAMPLE 1

A 1% solution of carbamide peroxide was prepared in an alcohol-propylene glycol carrier. Twice daily topical application of this solution were self-administered by a 26 year old female patient suffering from acne vulgaris. After two weeks of treatment the comedone count on the patient's face had declined from 28 to 15.

EXAMPLE 2

A 20 year-old male applied 10% carbamide peroxide prepared in an alcohol gel containing 6% polyoxyethylene lauryl ether four times daily. After 10 days the number of comedones on his face had declined from 43 to 25 and by the end of four weeks of treatment he had only 18 comedones on his face.

EXAMPLE 3

A 30 year-old female with acne vulgaris applied a 5% by volume solution of carbamide peroxide in a 70% ethyl alcohol and 30% propylene glycol carrier. The product was applied to all involved areas of the face and back twice daily. Before treatment this patient had 64 comedones on the face and back but after two weeks of treatment she had only 41 comedones in these areas.

EXAMPLE 4

A 2.5% carbamide peroxide cream was prepared containing water, propylene glycol, bentonite, glycerol stearate, isopropyl myristate and cellulose gum and applied twice daily to the skin of a 24 year-old male with many comedones on his forehead. After two weeks of such treatment the number of comedones on his forehead had declined from 28 to 12.

EXAMPLE 5

A 26 year-old male who had been unable to use 5 or 10% benzoyl peroxide preparations due to rashes each time he used them, applied a topical 5% carbamide peroxide preparation twice daily for eight weeks. The number of comedones declined over this treatment period from 46 to 29 at two weeks and to only 16 comedones after eight weeks of therapy.

EXAMPLE 6

An alcohol/aqueous solution containing 2.5% carbamide peroxide and 6% erythromycin was applied topically twice daily by a 30 year-old female with acne vulgaris consisting of both comedones (18) and papules and pustules(12). After four weeks of treatment the patient's face was considerably clearer with only 8 comedones and 6 papules or pustules apparent.

EXAMPLE 7

A 14 year-old female with several comedones and 15 small acne pustules and papules applied a solution comprised of 10% carbamide peroxide and 2% erythromycin in an alcohol-propylene glycol carrier. After 8 weeks of one to twice daily treatment the subject's face was free of all but 2 small acne papules.

EXAMPLE 8

A alcohol-propylene glycol vehicle containing 5% carbamide peroxide and 2% nicotinamide was applied four times daily by a 21 year-old male with a mixture of comedones and papulo-pustules on his face. After ten days of treatment his face was much improved and after four weeks of such treatment, it was almost completely clear.

EXAMPLE 9

A 16 year-old male with moderate severe inflammatory acne consisting of primarily papules and pustules as well as a lessor number of comedones applied a gel containing 15% carbamide peroxide and 10% nicotinamide twice daily. The patient's lesions almost completed cleared within ten (10) days but he had to discontinue the product because of excessive chapping.

EXAMPLE 10

Carbamide peroxide 5% and clindomycin phosphate 1% were incorporated into an alcoholic gel containing 6% polyoxyethylene lauryl ether and applied to the face twice daily by a 22 year-old male with acne vulgaris. This patient's comedone count decreased from 26 to 10 and the papulo-pustule count from 16 to 8 after 4 weeks of such treatment.

EXAMPLE 11

An aqueous/alcohol solution containing 10% carbamide peroxide and 2.5% clindamycin phosphate was applied once daily by a 24 year-old female with acne comedones, papules and pustules on her face. After two weeks of treatment she was noted to have greater than a 40% reduction in both comedones as well as papulopustules.

EXAMPLE 12

An aqueous/alcohol solution containing a salt of tetracyline such as tetracycline hydrochloride is also useful in amounts of about 1% to about 5% by volume of the carrier when combined with an effective amount of carbamide peroxide.

The present invention includes within the scope thereof pharmaceutical compositions suitable for topical administration having as an active ingredient thereof carbamide peroxide, the chemical formula of which is:

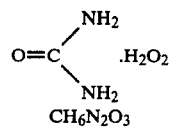

$$CH_6N_2O_3$$

Also included in the scope of the invention is the combination of carbamide peroxide with one or more of nicotinic acid or nicotinamide or a topical antibiotic such as erythromycin base, clindamycin phosphate and tetracycline hydrochloride. Where appropriate a pharmaceutically acceptable carrier gel, or ointment is employed.

Liquid dosage forms for topical administration includes acceptable emulsions, solutions and suspensions containing volatile diluents commonly used in the art, such as alcohol, glycol and the like. Besides such diluents, topically applied compositions may also include wetting agents, emulsifying and suspending agents.

It will be apparent to those skilled in the art that only the preferred embodiments have been described by way of exemplification and that there are various modifications and alterations therein which fall in the scope of this invention and are intended to be covered by the claims appended hereto.

What is claimed is:

1. A method of decreasing open and closed comedones of acne vulgaris in human patients having such comedones comprising topically administering a therapeutically effective amount of carbamide peroxide to a patient having such open and closed comedones.

2. The method of claim 1, wherein said carbamide peroxide is dispersed in a pharmaceutically acceptable carrier.

3. The method of claim 2, wherein the carbamide peroxide is present in the amount of not less than about 1% by volume of the carrier.

4. The method of claim 2, wherein the carbamide peroxide is present in the range of between about 1% and about 15% by volume of the carrier.

5. The method of claim 2, wherein the carrier is selected from an alcohol or a glycol or mixtures thereof.

6. A method of decreasing the inflammatory lesions of acne vulgaris in human patients having such inflammatory lesions comprising topically administering to a patient having such inflammatory lesions a therapeutically effective amount of carbamide peroxide in combination with a therapeutically effective amount of one or more of a topical antibiotic, nicotinic acid or nicotinamide.

7. The method of claim 6, wherein the effective ingredients are dispersed in a pharmacuetically acceptable carrier.

8. The method of claim 7, wherein the effective ingredients include erythromycin base present in the range of from about 1% to about 6% by volume of the carrier.

9. The method of claim 7, wherein the effective ingredients include clindamycin phosphate present in the range of from about 1% to about 5% by volume of the carrier.

10. The method of claim 7, wherein the effective ingredients include tetracycline hydrochloride present in the range of from about 1% to about 5% by volume.

11. The method of claim 7, wherein the effective ingredients include nicotinamide present in the range of from about 1% to about 10% by volume of the carrier.

* * * * *